(12) United States Patent
Rigoard et al.

(10) Patent No.: US 10,058,280 B2
(45) Date of Patent: Aug. 28, 2018

(54) MAPPING METHOD AND SYSTEM, METHOD AND SYSTEM FOR EVALUATING THE EFFICACY OF MEDULLARY STIMULATION

(71) Applicant: Centre Hôspitalier Universitaire de Poitiers, Poitiers (FR)

(72) Inventors: Philippe Rigoard, Poitiers (FR); Farid Guetarni, Chauvigny (FR)

(73) Assignee: CENTRE HÔSPITALIER UNIVERSITAIRE DE POITIERS, Poitiers (FR)

( * ) Notice: Subject to any disclaimer, the term of this patent is extended or adjusted under 35 U.S.C. 154(b) by 0 days.

(21) Appl. No.: 15/021,337

(22) PCT Filed: Aug. 12, 2014

(86) PCT No.: PCT/EP2014/067231
§ 371 (c)(1),
(2) Date: Mar. 11, 2016

(87) PCT Pub. No.: WO2015/036191
PCT Pub. Date: Mar. 19, 2015

(65) Prior Publication Data
US 2016/0220181 A1  Aug. 4, 2016

(30) Foreign Application Priority Data
Sep. 13, 2013 (FR) .................................. 13 58850

(51) Int. Cl.
*G06T 11/80* (2006.01)
*A61B 5/00* (2006.01)
(Continued)

(52) U.S. Cl.
CPC .......... *A61B 5/4848* (2013.01); *A61B 5/1072* (2013.01); *A61B 5/4824* (2013.01);
(Continued)

(58) Field of Classification Search
CPC ..... A61B 5/4824; A61B 5/4827; G06T 11/80; G06T 11/203
(Continued)

(56) References Cited

U.S. PATENT DOCUMENTS 7,374,536 B1 * 5/2008 Taylor ..................... A61B 5/00
600/300
8,046,241 B1 * 10/2011 Dodson ................ G06F 19/363
705/2
(Continued)

OTHER PUBLICATIONS

North, Richard B., et al. "Automated 'pain drawing' analysis by computer-controlled, patient-interactive neurological stimulation system." Pain 50.1 (1992): 51-57.*
(Continued)

*Primary Examiner* — Diane Wills
(74) *Attorney, Agent, or Firm* — Pillsbury Winthrop Shaw Pittman LLP (57) ABSTRACT

A method for mapping painful zones, includes: on a first screen, displaying a first silhouette representing the rear face of a body; drawing at least one painful zone on the first displayed silhouette; indicating the location of a pain felt by a patient; determining a first number of pixels on the first screen corresponding to the painful zone; measuring a reference distance between two morphological reference points on the patient; converting the first number of pixels into a painful cutaneous surface, the reference distance being used as a parameter in the conversion.

13 Claims, 5 Drawing Sheets

(51) Int. Cl.
- A61B 5/107 (2006.01)
- A61B 7/04 (2006.01)
- A61N 1/36 (2006.01)
- G06T 11/60 (2006.01)
- G06F 3/0482 (2013.01)
- G06F 3/0484 (2013.01)
- G06F 3/0488 (2013.01)
- G06T 11/00 (2006.01)
- G06T 11/20 (2006.01)
- G06T 11/40 (2006.01)
- G06F 3/0481 (2013.01)
- G09G 5/14 (2006.01)
- G16H 40/63 (2018.01)
- G16H 10/20 (2018.01)

(52) U.S. Cl.
CPC .......... *A61B 5/4827* (2013.01); *A61B 5/7435* (2013.01); *A61B 7/04* (2013.01); *A61N 1/36071* (2013.01); *G06F 3/0481* (2013.01); *G06F 3/0482* (2013.01); *G06F 3/04842* (2013.01); *G06F 3/04845* (2013.01); *G06F 3/04883* (2013.01); *G06T 11/001* (2013.01); *G06T 11/206* (2013.01); *G06T 11/40* (2013.01); *G06T 11/60* (2013.01); *G06T 11/80* (2013.01); *G09G 5/14* (2013.01); *G16H 40/63* (2018.01); *G06F 2203/04803* (2013.01); *G06T 2207/30004* (2013.01); *G06T 2207/30196* (2013.01); *G06T 2210/62* (2013.01); *G06T 2215/16* (2013.01); *G09G 2320/0693* (2013.01); *G09G 2380/08* (2013.01); *G16H 10/20* (2018.01)

(58) Field of Classification Search
USPC .......................... 345/689; 600/554; 715/211
See application file for complete search history.

(56) References Cited

U.S. PATENT DOCUMENTS

| | | |
|---|---|---|
| 2001/0007950 A1 | 7/2001 | North et al. |
| 2009/0005649 A1 | 1/2009 | Baird et al. |
| 2015/0154453 A1* | 6/2015 | Wilf .................. G06K 9/00711 382/103 |

OTHER PUBLICATIONS

International Search Report as issued in International Patent Application No. PCT/EP2014/067231, dated Oct. 29, 2014.

* cited by examiner

MAPPING METHOD AND SYSTEM, METHOD AND SYSTEM FOR EVALUATING THE EFFICACY OF MEDULLARY STIMULATION

CROSS-REFERENCE TO RELATED APPLICATIONS

This is the U.S. National Stage of PCT/EP2014/067231, filed Aug. 12, 2014, which in turn claims priority to French Patent Application No. 1358850, filed Sep. 13, 2013, the entire contents of all applications are incorporated herein by reference in their entireties.

TECHNICAL FIELD OF THE INVENTION

The invention relates to the medical field, and notably to the technique of medullary stimulation, in particular for the management of post-operational spinal pathology. The invention more particularly relates to systems and methods for mapping dorsal pain felt by a patient, and paraesthesias felt following medullary stimulation aiming to relieve said pains.

TECHNOLOGICAL BACKGROUND OF THE INVENTION

The technique of medullary stimulation, also known as stimulation of the spinal cord or neurostimulation, is used to provide relief to patients suffering from severe neuropathic pain. This technique consists in emitting electric pulses in the direction of the nerve fibres of the spinal cord of a patient, through the intermediary of at least one multi-contact electrode. The at least one electrode may be old generation (mono-column) or new generation (multi-column).

Medullary stimulation may be applied by surgical or percutaneous route (in this case, the central nervous system is stimulated; the stimulation is triggered from the electrode in the vertebral canal) or instead it may be sub-cutaneous nervous stimulation (the peripheral nervous system is then stimulated). To do so, the electrode has been surgically implanted beforehand on the spinal cord, or in sub-cutaneous tissues, at the level of the painful zone. "At the level of the painful zone" is taken to mean:

for sub-cutaneous stimulation, in a region of the painful zone for medullary, percutaneous or surgical stimulation, with regard to a certain region of the spinal cord in the vertebral canal, at the level of which are centralised the projections pertaining to a painful peripheral cutaneous zone (for example, a painful region of the lower limb is projected onto the level of the medullary region, situated at the level of the thoracic vertebrae T9 to T11).

The electrode is connected to a control box making it possible to activate the pads of the electrode in order to generate a controlled electric field. The electric field stimulates a neuronal population, which causes a paraesthesia leading to a relief of the pain.

The choice of the electrode(s) is crucial. In fact the results are variable as a function of the therapeutic tool used (more or less sophisticated electrodes; percutaneous or surgical electrodes, conventional or new generation electrodes, mono-column or multi-column electrodes, surface electrodes of more or less limited cover, etc.). The choice of the therapeutic tool is made as a function of pain quantification parameters, such as the size or instead the location of the painful zone. In fact, the evaluation of these parameters is a key step, making it possible to choose appropriately the electrode(s) to implant.

GENERAL DESCRIPTION OF THE INVENTION

The invention proposes a method for evaluating said pain quantification parameters.

The invention thus essentially relates to a method for mapping painful zones, including the following steps:

Displaying a first silhouette representing the rear face of a body, on a first screen Drawing at least one painful zone on said first displayed silhouette, indicating the location of a pain felt by a patient Determining a first number of pixels on the first screen, corresponding to said painful zone Measuring a reference distance between two morphological reference points on the patient Converting said first number of pixels into a painful cutaneous surface, said reference distance being used as a parameter in said conversion.

The cutaneous surface corresponding to the painful zone drawn by the patient is a first pain quantification parameter for which the method enables the evaluation. This first parameter helps to choose appropriately the therapeutic tool, i.e. the electrode, to use. In fact, if the cutaneous surface is 25 square centimeters, an electrode with a coverage of 10 square centimeters could be considered unsuitable. It may be noted that, advantageously, the screen is a touch screen, and the patient draws the painful zone with his fingers, which is more practical than using a mouse or a stylet.

At each touch pressure a delimitation by circling of the painful zone is captured at the mapping level, several zones being able to be drawn with or without superposition. This mapping is calibrated with respect to the reference distance in order to extrapolate the plots with respect to the individual concerned. The drawing is simple, quick to carry out and in addition makes it possible to delimit a surface, to identify a location and an evolution of the plot as the pain is treated.

Apart from the characteristics which have been evoked in the preceding paragraph, the mapping method according to the invention may have one or more additional characteristics among the following, considered individually or according to any technically possible combinations thereof.

In a non-limiting embodiment, the morphological reference points are the iliac crests of the patient. In fact, they are invariant reference points depending on the corpulence of the patient.

In a non-limiting embodiment, the mapping method includes the following step: correcting the converted painful cutaneous surface with the aid of a correction coefficient. This step is based on the Bland Altman test. This test is a statistical test making it possible to make up for the intra-individual error of appreciation of the plot by the operator (the patient or the clinician). A phase of taking measurements with exact surfaces different in shape and location has been carried out on a sample of significant size. Then comparisons between the drawn surfaces and the actual surfaces have made it possible to define a correction coefficient (corresponding to the standard deviation of the difference of averages observed).

In a non-limiting embodiment, the mapping method includes the following step: determining a ratio of painful cutaneous surface comprised in a region of the first silhouette. Said ratio of cutaneous surface comprised in the region is a second pain quantification parameter for which the method enables the evaluation. In fact, it is interesting to relate the painful cutaneous surface to known topographical notions of the organism, notably delimitations approved by specialized organizations such as the delimitations High Back/Low Back, or instead commonly accepted delimitations in anatomical terms, such as dermatomes. By correlating the location of the painful cutaneous surface with a chosen topographical frame of reference, the physician has access to data allowing him to choose appropriately his therapeutic tools, i.e. the electrodes to implant. For example, an electrode may be efficacious in a given region, and inefficacious in another. It may be noted that the quantification of pain by topographic surface is important for determining the predominance and the intensity of certain types of pain and thus explain the pain by a determinism linked to the nerve roots. This step thus moreover makes it possible to determine the nerve roots which are more or less involved in the pain mechanism.

In a non-limiting embodiment, the region corresponds to a dermatome. A dermatome is a strip of skin which corresponds to a selective innervation of a given nerve of the organism. Thanks to the mapping method according to the invention, the physician has access to the percentages of the painful cutaneous surface comprised in each dermatome. In another non-limiting embodiment, the region corresponds to a lumbar region.

In a non-limiting embodiment, the step of drawing at least one painful zone comprises the following sub-steps:
    Drawing in a first manner a neuropathic pain;
    Drawing in a second manner a mechanical pain.

In fact, certain scientists consider that medullary stimulation is not efficacious for mechanical pain. These sub-steps can make it possible to confirm or invalidate this consideration.

The invention also relates to a method for evaluating the efficacy of medullary stimulation, including the following steps:
    Displaying a second silhouette representing the rear face of a body, on a second screen
    Drawing at least one paraesthesia zone on said second displayed silhouette, indicating the location of a paraesthesia felt by the patient in response to medullary stimulation
    Determining a second number of pixels on the second screen, corresponding to said paraesthesia zone
    Converting said second number of pixels into a paraesthesic cutaneous surface, the reference distance being used as a parameter in said conversion.
    Comparing the paraesthesic cutaneous surface with a painful cutaneous surface determined beforehand.

It may be noted that in a non-limiting embodiment, the second screen is the aforementioned first screen. In a non-limiting embodiment, the second screen is a touch screen and the patient draws the paraesthesia zone with his fingers. In a non-limiting embodiment, the second silhouette is substantially identical to the aforementioned first silhouette. Advantageously, the painful surface has been predetermined using the aforementioned mapping method.

By comparing the paraesthesic cutaneous surface and the painful cutaneous surface, the physician can determine whether the medullary stimulation has been efficacious. In fact, the medullary stimulation has been efficacious if the paraesthesic cutaneous surface is substantially equal to the painful cutaneous surface.

The mapping method according to the invention thus makes it possible to determine pain quantification parameters:

in a strict manner, by calculation of the painful surface, and
in an indirect manner, by evaluation of the surface of the paraesthesias and finally the pain/paraesthesias ratio.

All of this is carried out as a function of the zones and somatotopic territories of the nerve fibres.

The two aspects of the invention may be noted:
    a method for evaluating a painful surface with regard to a medical device with a view to evaluating the efficacy thereof;
    a diagnostic and therapeutic method (pre, during and post-operation) making it possible to collect and to monitor the pain of the patient and its evolution, and to enable indication towards a therapeutic of choice: it can be considered as a medullary electronic stethoscope.

Apart from the characteristics that have been mentioned in the preceding paragraph, the method for evaluating the efficacy of medullary stimulation according to the invention may have one or more additional characteristics among the following, considered individually or according to any technically possible combinations thereof.

In a non-limiting embodiment, the comparison step comprises the following sub-step:
    Calculating a percentage coverage of the painful cutaneous surface by the paraesthesic cutaneous surface.

The physician may thus evaluate numerically the efficacy of the medullary stimulation.

In a non-limiting embodiment, the method for evaluating the efficacy of medullary stimulation comprises the following steps:
    Superimposing the second silhouette on a first silhouette including the painful zones.

Advantageously, the painful zones have been drawn beforehand on the first silhouette via the aforementioned mapping method. Advantageously, the first silhouette and the second silhouette are substantially identical. It is thus easy to know in which painful zones medullary stimulation has been efficacious.

In a non-limiting embodiment, the medullary stimulation is carried out during an operation of implantation of said electrode. This is particularly advantageous for implanting the electrode at a spot where the medullary stimulations will be efficacious. In practice, the patient is woken up during the implantation operation, and indicates to the physician, thanks to the method for evaluating the efficacy of medullary stimulation according to the invention, whether the electrode is placed at an appropriate spot. If this is not the case, the physician may then move the electrode before putting the patient back to sleep and finishing the implantation operation.

In a non-limiting embodiment, the medullary stimulation is carried out after an operation of implantation of said electrode, for example several months or several years after the operation. This makes it possible to check that the patient responds correctly to medullary stimulations, and that the painful zone is always covered by the paraesthesia zone. In fact, it is sometimes observed that the paraesthesias die down over time, or even disappear. Thus, monitoring of the patient is possible.

The invention also proposes a mapping system, including:
    Means for displaying a silhouette representing the rear face of a body, on a screen
    Means for drawing at least one zone on said silhouette
    Means for determining a number of pixels on the screen, corresponding to said zone Means for converting said number of pixels into a cutaneous surface, by means of a reference distance being used as a parameter in said conversion.

The drawn zones may correspond to painful zones or to paraesthesia zones felt following medullary stimulation.

Apart from the characteristics which have been evoked in the preceding paragraph, the mapping system according to the invention may have one or more additional characteristics among the following, considered individually or according to any technically possible combinations thereof.

In a non-limiting embodiment, the mapping system includes:
Means for correcting the cutaneous surface using a correction criterion.

In a non-limiting embodiment, the mapping system includes:
Means for determining a ratio of said cutaneous surface comprised in a region of the silhouette.

In a non-limiting embodiment, the mapping system includes:
Means for comparing the cutaneous surface with a second cutaneous surface determined beforehand.

The mapping system thus makes it possible to compare a painful cutaneous surface with a paraesthesia cutaneous surface, the paraesthesias being felt in response to medullary stimulation.

The invention also proposes a system for evaluating the efficacy of medullary stimulation, including:
The mapping system described previously
Medullary stimulation means
Means for comparing a painful cutaneous surface with a paraesthesic cutaneous surface, said paraesthesia being felt in response to medullary stimulation by the medullary stimulation means.

Conventionally, the medullary stimulation means comprise at least one multi-contact electrode connected to a control box, said electrode being implanted at the level of painful zones of the patient.

In a non-limiting embodiment, the system for evaluating the efficacy of medullary stimulation includes:
Means for calculating a percentage coverage of the painful cutaneous surface by the paraesthesic cutaneous surface.

The invention and its different applications will be better understood on reading the description that follows and by examining the accompanying figures.

BRIEF DESCRIPTION OF THE FIGURES

The figures are only presented for indicative purposes and in no way limit the invention. The figures show.

DETAILED DESCRIPTION OF AT LEAST ONE EMBODIMENT OF THE INVENTION

Unless stated otherwise, a same element appearing in the different figures has a single reference.

The invention proposes a method for mapping painful zones, a method for evaluating the efficacy of medullary stimulation, a mapping system, and a system for evaluating the efficacy of medullary stimulation.

The mapping method is intended to:
indicate the location of pains felt by a patient,
indicate the type of said pains (neuropathic or mechanical) felt, and
provide the characteristics of said pains. These characteristics are notably the cutaneous surface concerned by the pain, and the percentage of painful cutaneous surface comprised in each dermatome or each lumbar region.

These results allow a physician to choose one or more electrodes to implant at the level of the painful zone(s), in order to implement the technique of medullary stimulation aiming to relieve the pain of the patient. In fact, as a function of the characteristics indicated previously, certain electrodes will be more or less suitable.

Figure 1:
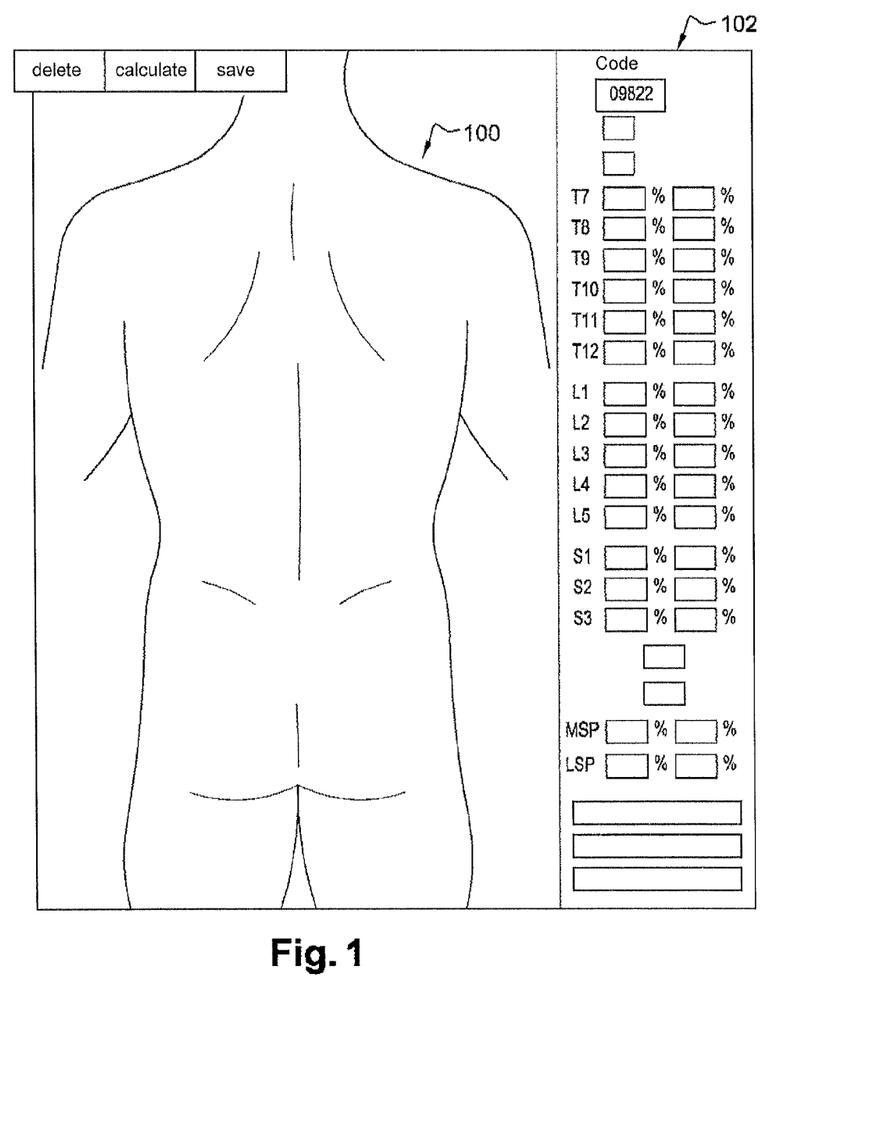
In FIG. 1, a step of displaying a silhouette on a screen, according to an embodiment of the mapping method according to the invention.
Figure 4:
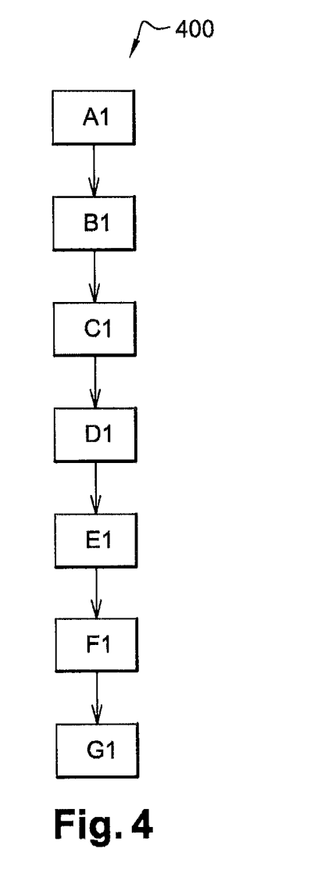
In FIG. 4, the steps of an embodiment of the mapping method according to the invention.

More precisely, with reference to FIG. 4, the mapping method 400 comprises the following steps:

A1: with reference to FIG. 1, displaying a first silhouette 100 representing the rear face of a body, on a first screen 102. The first screen 102 is for example a touch screen, advantageously a tablet touch screen. In fact, a touch screen enables ergonomic use, and a touch tablet is of sufficiently large size to enable an agreeable display, and sufficiently small to limit bulk. In the embodiment described, the silhouette 100 is a standard model, not suited to the morphology of the patient. However, an embodiment in which the silhouette 100 has a shape suited to the morphology of the patient is not excluded.

Figure 2:
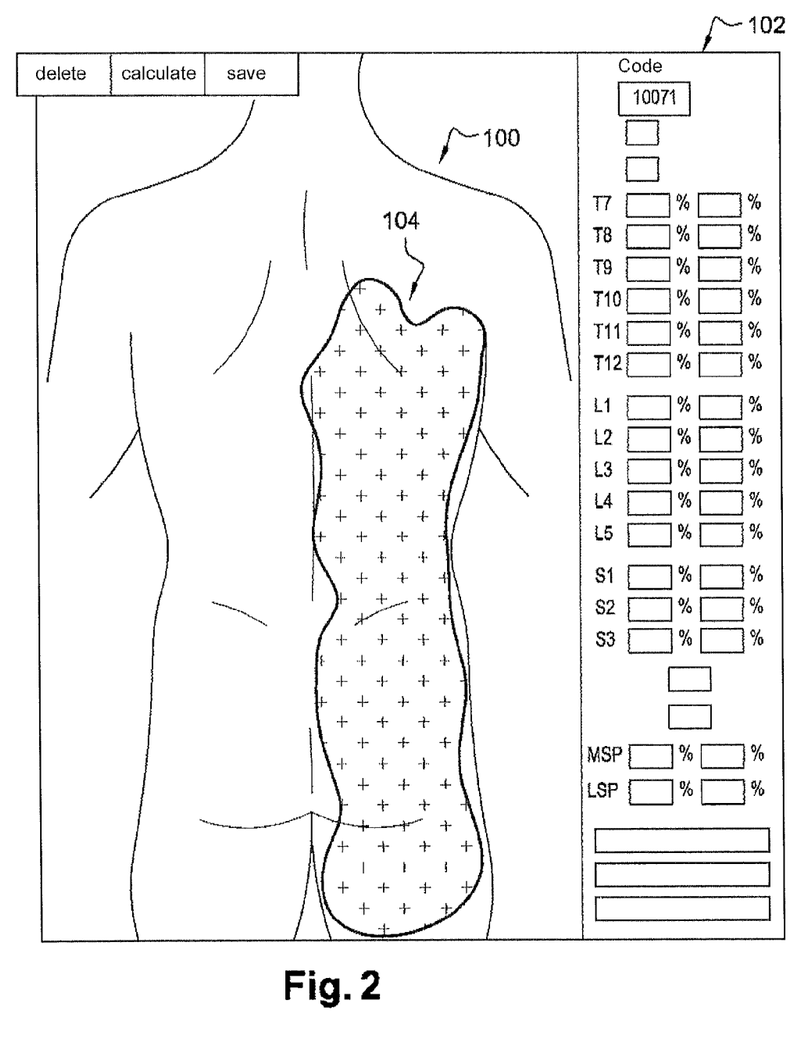
In FIG. 2, a step of drawing a painful zone on said silhouette, according to an embodiment of the mapping method according to the invention.

B1: with reference to FIG. 2, drawing at least one painful zone 104 on said first displayed silhouette 100, indicating the location of a pain felt by the patient. In a non-limiting embodiment in which the screen 102 is a touch screen, the patient delimits the painful zone 104 by circling it with his finger. In an embodiment, the patient has at his disposal a palette of two colours, each colour representing a type of pain. In another embodiment, the pain is represented by a single and same colour but hatching makes it possible to differentiate the type of pain. Type of pain is taken to mean mechanical or neuropathic pain. Determined criteria grouped together in a questionnaire make it possible to qualify neuropathic pain. The patient may thus indicate whether a painful zone corresponds to neuropathic pain or to mechanical pain.

C1: determining a first number of pixels on the first screen 102, corresponding to the painful zone 104. It may be noted that the numbers of pixels corresponding to neuropathic and mechanical pains, or to different painful zones, are added together except in the case of an intersection: in this case, the common surface is only counted once.

D1: measuring a reference distance on the patient. In the embodiment described, the reference distance corresponds to the distance between the two iliac crests of the patient. In fact, this distance has the advantage of being invariant depending on the corpulence of the patient. It may be noted that other morphological reference points could be used, for example the distance between the shoulder blades or the distance between the mastoids, but the distance between the iliac crests is preferred. It is understood that the step of measuring the reference distance may be carried out before the steps described previously, or between two of said steps.

E1: converting the first number of pixels into a painful cutaneous surface, the reference distance being used as a parameter in the conversion. The painful cutaneous surface is then displayed on the first screen 102, which allows the physician to have the information at his disposal. The painful cutaneous surface is for example expressed in square centimeters.

To carry out this conversion step, two coefficients are calculated:
 a vertical coefficient equal to the actual size of the patient divided by the number of pixels representing the size of the silhouette
 a horizontal coefficient equal to the distance between the iliac crests of the patient divided by the number of pixels representing the distance between the iliac crests on the silhouette.

The painful cutaneous surface is then equal to the product of the horizontal coefficient, the vertical coefficient and the first number of pixel corresponding to the painful zone.

Figure 3:
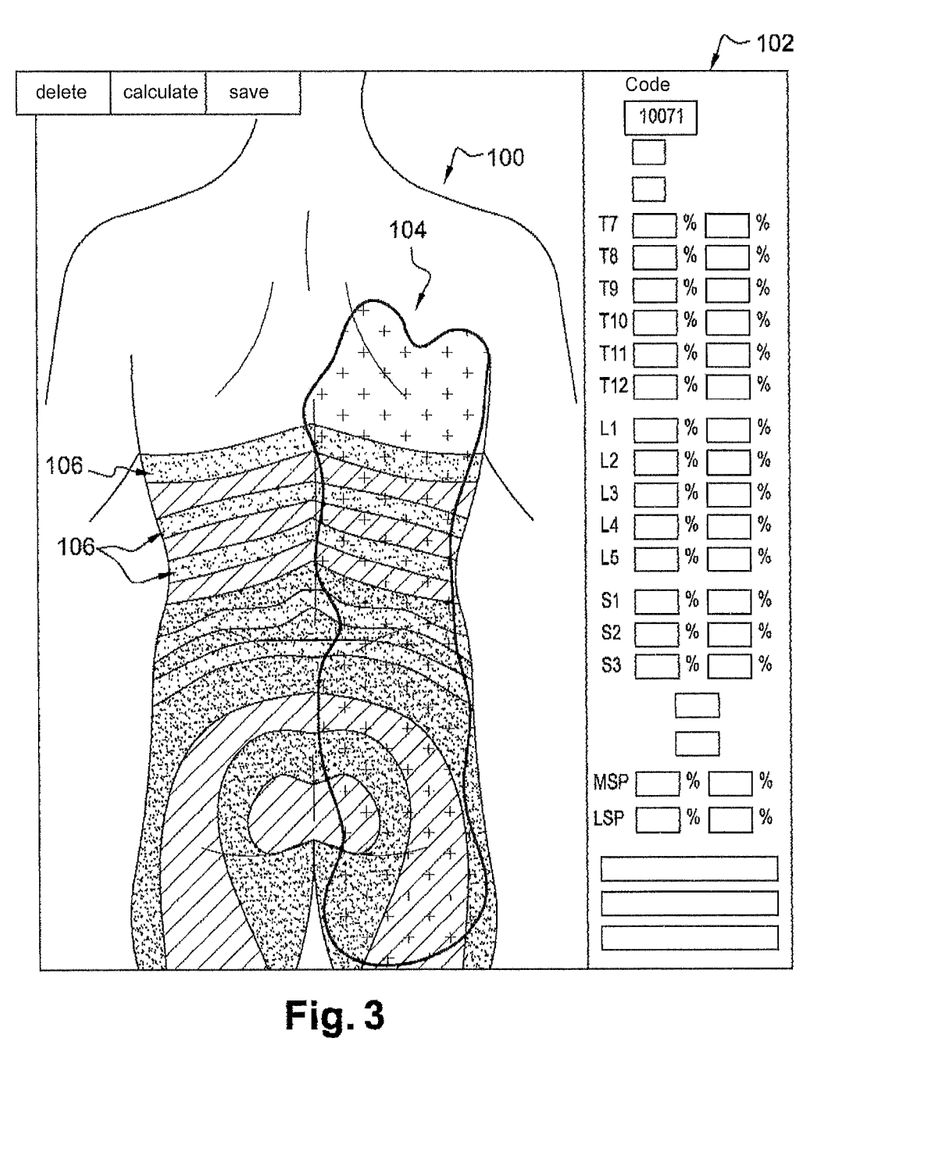
In FIG. 3, a step of displaying dermatomes on the silhouette, and calculating ratios of painful cutaneous surface corresponding to each of said dermatomes.

F1: determining a ratio of painful cutaneous surface comprised in a region 106 of the first silhouette 100. With reference to FIG. 3, in an embodiment, the considered region 106 corresponds to a dermatome. In an embodiment, the regions 106 are displayed on the silhouette 100, superimposed on the drawn painful zone 104. The region 106 could also be a lumbar region, or any other region corresponding to a known topographic notion. Advantageously, several ratios corresponding to several regions 106 of a topographical frame of reference are calculated. In an embodiment, these ratios are expressed in percentage in order to facilitate the reading thereof. The physician can thus know which dermatomes are engaged by the pain, and in which proportions. In an embodiment, a correspondence table is displayed beside the first silhouette 100, showing the ratios or the percentages of painful cutaneous surface by considered region. The painful cutaneous surface is thus expressed in percentages with respect to the surface representation of the different dermatomes of the dorsolumbar region in particular.

G1: in an embodiment, the first silhouette 100 on which the painful zone(s) 104 are drawn, as well as the characteristics of said pains, are saved on a server.

The mapping method 400 may be implemented at different moments in temporal space for a given patient. An initial mapping and follow-up mappings are thereby obtained, which makes it possible to compare the painful region before and after the patient has received a given treatment and in particular a medullary stimulation implantation. The evaluations may also be repeated over time and at several moments of the day which makes it possible, by data implementation, to arrive at an averaged approximation of the painful regions that is more accurate over time.

The method for evaluating the efficacy of medullary stimulation is used for:
During an operation of implantation of one or more electrodes in the patient, to know whether the electrode is correctly positioned or if it is advantageous to move it, and/or post-operationally, to monitor the patient, i.e. checking 19 that the medullary stimulation is (still) efficacious, and whether it in fact relieves the patient over the whole of the painful zones.

Figure 5:
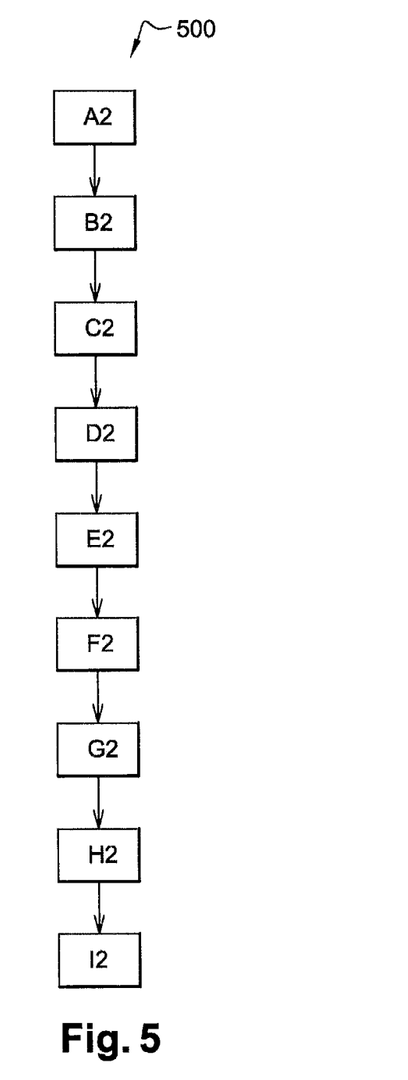
In FIG. 5, the steps of a method for evaluating the efficacy of medullary stimulation according to an embodiment of the invention.

More precisely, with reference to FIG. 5, the method for evaluating the efficacy of medullary stimulation 500 comprises the following steps:

A2: carrying out the steps of the mapping method 400 described previously.

B2: carrying out medullary stimulation of the patient with at least one electrode. In an embodiment, the electrode has been implanted beforehand during a surgical operation at the level of the painful zone 104 felt by the patient. In another embodiment, the medullary stimulation is carried out during a surgical operation intended to implant the electrode.

C2: displaying a second representative silhouette substantially identical to the first silhouette 100, on a second screen. The second screen is for example a touch screen, advantageously a touch tablet screen. In a non-limiting embodiment, the second screen is the first screen evoked previously.

D2: drawing at least one paraesthesia zone on the second displayed silhouette, indicating the location of a paraesthesia felt by the patient in response to medullary stimulation.

E2: determining a second number of pixels on the second screen, corresponding to the paraesthesia zone.

F2: converting the second number of pixels into a paraesthesia cutaneous surface, the aforementioned reference distance being used as a parameter in the conversion. The conversion is carried out in the same way as at E1 of the mapping method 400. The paraesthesic cutaneous surface is then displayed on the second screen, which allows the physician to have the information at his disposal.

G2: comparing the paraesthesic cutaneous surface with the painful cutaneous surface determined during step E1 of the mapping method 400.

H2: superimposing the second silhouette and the first silhouette 100 on the second screen or on the first screen 102.

I2: in an embodiment, the second silhouette on which the paraesthesia zone(s) are drawn, as well as the paraesthesic cutaneous surface, are saved on the server.

Figure 6:
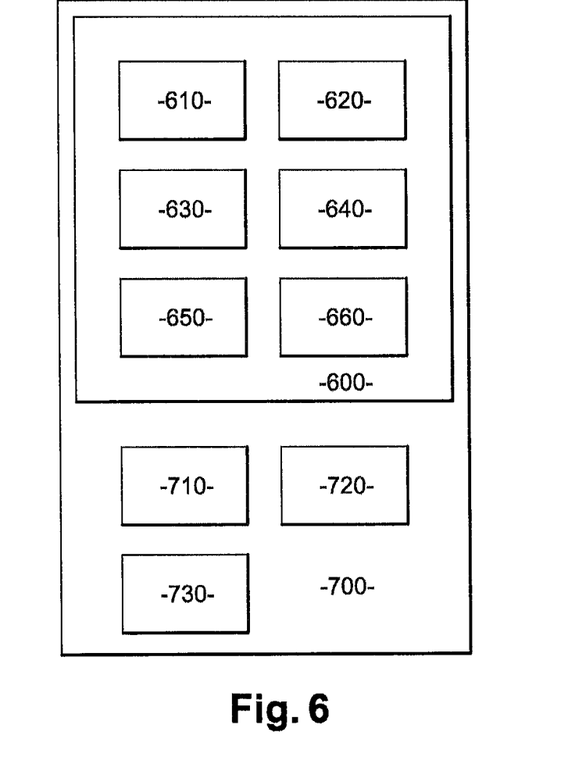
In FIG. 6, a schematic representation of a mapping system and a system for evaluating the efficacy of medullary stimulation according to an embodiment of the invention.

With reference to FIG. 6, the mapping system 600 includes:
Means for displaying 610 a silhouette representing the rear face of a body, on a screen
Means for drawing 620 at least one zone on said silhouette
Means for determining 630 a number of pixels on the screen, corresponding to said zone
Means for converting 640 said number of pixels into a cutaneous surface, by means of a reference distance being used as a parameter in said conversion.
Means for determining 650 a ratio of said cutaneous surface comprised in a region of the silhouette
Means for comparing 660 the cutaneous surface with a second cutaneous surface determined beforehand.

The mapping system 600 makes it possible to implement the mapping method 400 according to the invention. The zones drawn may correspond to painful zones or to paraesthesia zones felt following medullary stimulation.

The system for evaluating the efficacy of medullary stimulation 700 comprises:

The mapping system 600

Medullary stimulation means 710. Conventionally, it involves at least one multi-contact electrode implanted under the skin of the patient, connected to a control box.

Means for comparing 720 a painful cutaneous surface with a paraesthesic cutaneous surface, said paraesthesia being felt in response to medullary stimulation by the medullary stimulation means Means for calculating 730 a percentage coverage of the painful cutaneous surface by the paraesthesic cutaneous surface.

The system for evaluating the efficacy of medullary stimulation 700 makes it possible to implement the method for evaluating the efficacy of medullary stimulation 500.

The invention claimed is:

1. A method for mapping and treating painful zones, comprising:
    displaying, using an electronic mapping system, a first silhouette representing the rear face of a body, on a first screen of the electronic mapping system;
    drawing, using the electronic mapping system, at least one painful zone on said first displayed silhouette, indicating a location of a pain felt by a patient;
    determining, using the electronic mapping system, a first number of pixels on the first screen, corresponding to said painful zone;
    measuring a reference distance between two morphological reference points on the patient, said reference distance being selected to be invariant depending on a corpulence of the patient;
    wherein said reference distance is a distance between the iliac crests of the patient;
    converting, using the electronic mapping system, said first number of pixels into a painful cutaneous surface, said reference distance being used as a parameter in said conversion,
    selecting at least one electrode based on the painful cutaneous surface obtained by said conversation; and emitting electric pulses with the selected at least one electrode in said painful zone,
    wherein said converting includes
    calculating, using the electronic mapping system, a vertical coefficient equal to an actual size of the patient divided by a number of pixels representing the size of the silhouette;
    calculating, using the electronic mapping system, a horizontal coefficient equal to said reference distance divided by a number of pixels representing the distance between the iliac crests on the silhouette.

2. The method according to claim 1, further comprising:
    correcting, using the electronic mapping system, the converted painful cutaneous surface with the aid of a correction coefficient.

3. The method according to claim 1, further comprising:
    determining, using the electronic mapping system, a ratio of painful cutaneous surface comprised in a region of the first silhouette.

4. The method according to claim 1, wherein drawing the at least one painful zone comprises:
    drawing, using the electronic mapping system, in a first manner a neuropathic pain; and
    drawing, using the electronic mapping system, in a second manner a mechanical pain.

5. A method for evaluating the efficacy of medullary stimulation, comprising:
    performing a method for mapping and treating painful zones according to claim 1, said performing providing a reference distance between two morphological reference points on the patient;
    displaying, using the electronic mapping system, a second silhouette representing the rear face of a body, on a second screen of the electronic mapping system;
    drawing, using the electronic mapping system, at least one paraesthesia zone on said second displayed silhouette, indicating the location of a paraesthesia felt by the patient in response to medullary stimulation;
    determining, using the electronic mapping system, a second number of pixels on the second screen, corresponding to said paraesthesia zone;
    converting, using the electronic mapping system, said second number of pixels into a paraesthesic cutaneous surface, the reference distance being used as a parameter in said conversion, and
    comparing, using the electronic mapping system, the paraesthesic cutaneous surface with a painful cutaneous surface determined by said performing.

6. The method for evaluating the efficacy of medullary stimulation according to claim 5, wherein the comparing comprises:
    calculating, using the electronic mapping system, a percentage coverage of the painful cutaneous surface by the paraesthesic cutaneous surface.

7. The method according to claim 1, wherein the painful cutaneous surface is determined by multiplying said vertical coefficient, said horizontal coefficient and said determined first number of pixels.

8. A mapping system configured to map painful zones, the mapping system comprising:
    means for displaying a silhouette representing the rear face of a body, on a screen;
    means for drawing at least one painful zone on said silhouette to indicate a location of a pain felt by a patient;
    means for determining a number of pixels on the screen, corresponding to said zone, and
    means for converting said number of pixels on the screen into a painful cutaneous surface, by means of a reference distance being used as a parameter in said conversion, said reference distance being selected to be invariant depending on a corpulence of the patient;
    wherein said reference distance is a distance between the iliac crests of the patient;
    wherein the means for converting is configured to
    calculate a vertical coefficient equal to an actual size of the patient divided by a number of pixels representing the size of the silhouette;
    calculate a horizontal coefficient equal to a distance between said reference distance divided by a number of pixels representing the distance between the iliac crests on the silhouette; and
    multiply said vertical coefficient, said horizontal coefficient and said determined number of pixels on the screen.

9. The mapping system according to claim 8, further comprising:
    means for correcting the converted cutaneous surface by means of a correction coefficient.

10. The mapping system according to claim 8, further comprising:

means for determining a ratio of said cutaneous surface comprised in a region of the silhouette.

11. The mapping system according to claim 8, further comprising:
means for comparing the cutaneous surface with a second cutaneous surface determined beforehand.

12. A system for evaluating the efficacy of medullary stimulation, comprising:
the mapping system according to claim 8;
medullary stimulation means; and
means for comparing a painful cutaneous surface with a paraesthesic cutaneous surface, said paraesthesia being felt in response to medullary stimulation by the medullary stimulation means.

13. The system for evaluating the efficacy of medullary stimulation according to claim 12, further comprising:
means for calculating a percentage coverage of the painful cutaneous surface by the paraesthesic cutaneous surface.

* * * * *